United States Patent [19]

Turner et al.

[11] Patent Number: 5,408,017
[45] Date of Patent: Apr. 18, 1995

[54] HIGH TEMPERATURE POLYMERIZATION PROCESS USING IONIC CATALYSTS TO PRODUCE POLYOLEFINS

[75] Inventors: Howard W. Turner, Houston; Jo Ann M. Canich, Webster, both of Tex.; Bernard J. Folie, Zwijndrecht, Belgium

[73] Assignee: Exxon Chemical Patents Inc., Linden, N.J.

[21] Appl. No.: 77,479

[22] Filed: Jun. 14, 1993

Related U.S. Application Data

[63] Continuation-in-part of Ser. No. 898,638, Jun. 15, 1992, abandoned, Ser. No. 875,165, Apr. 28, 1992, Pat. No. 5,278,119, Ser. No. 542,236, Jun. 22, 1990, and Ser. No. 133,052, Dec. 21, 1987, abandoned, which is a continuation-in-part of Ser. No. 11,471, Jan. 30, 1987, abandoned, said Ser. No. 898,638, is a continuation-in-part of Ser. No. 737,611, Jul. 30, 1991, Pat. No. 5,198,401, which is a continuation-in-part of Ser. No. 555,977, Jul. 19, 1990, abandoned, which is a continuation-in-part of Ser. No. 133,480, Dec. 22, 1987, abandoned, which is a continuation-in-part of Ser. No. 8,800, Jan. 30, 1987, abandoned.

[51] Int. Cl.$^6$ ............................................. C08F 4/643
[52] U.S. Cl. ................................. 526/134; 526/127; 526/131; 526/160; 526/170; 526/348.6; 526/352; 502/155
[58] Field of Search ............... 526/127, 131, 134, 160, 526/170

[56] References Cited

U.S. PATENT DOCUMENTS

| | | | |
|---|---|---|---|
| 4,752,597 | 6/1988 | Turner | 502/104 |
| 5,026,798 | 6/1991 | Canich | 526/127 |
| 5,064,802 | 11/1991 | Stevens et al. | 502/155 |
| 5,084,534 | 1/1992 | Welborn, Jr. et al. | 526/160 |
| 5,153,157 | 10/1992 | Hlatky et al. | 502/117 |
| 5,198,401 | 3/1993 | Turner et al. | 502/155 |
| 5,278,119 | 1/1994 | Turner et al. | 502/155 |

FOREIGN PATENT DOCUMENTS

| | | |
|---|---|---|
| 0129368 | 12/1984 | European Pat. Off. |
| 277003 | 8/1988 | European Pat. Off. |
| 277004 | 8/1988 | European Pat. Off. |
| 0323454 | 7/1989 | European Pat. Off. |
| 0478913 | 4/1992 | European Pat. Off. |
| 0495375 | 7/1992 | European Pat. Off. |
| WO93/05082 | 3/1993 | WIPO |
| PCT/WO93/-08221 | 4/1993 | WIPO |

OTHER PUBLICATIONS

1297a Die Makromolekulare Chemie, Rapid Communications 13 (1992) Jan., No. 1, Basel, CH.
Periodic Table of The Elements as described by "Chemical and Engineering News", 63 (5), p. 27, 1985.

*Primary Examiner*—Joseph L. Schofer
*Assistant Examiner*—David Wu
*Attorney, Agent, or Firm*—M. S. Spiering; W. G. Muller

[57] ABSTRACT

This invention relates to a process for polymerizing olefins at high pressures in a polymerization medium at high temperature utilizing an ionic olefin polymerization catalyst derived from the reaction of a cyclopentadienyl-containing transition metal compound having a hydrolyzable alkyl or hydride ligand with an ion exchange activator. The ionic catalyst system has been found to be highly active at temperatures of 160° C. or greater, to provide a process capable of producing polymer products of desired chemical and physical properties at high production rates.

18 Claims, 3 Drawing Sheets

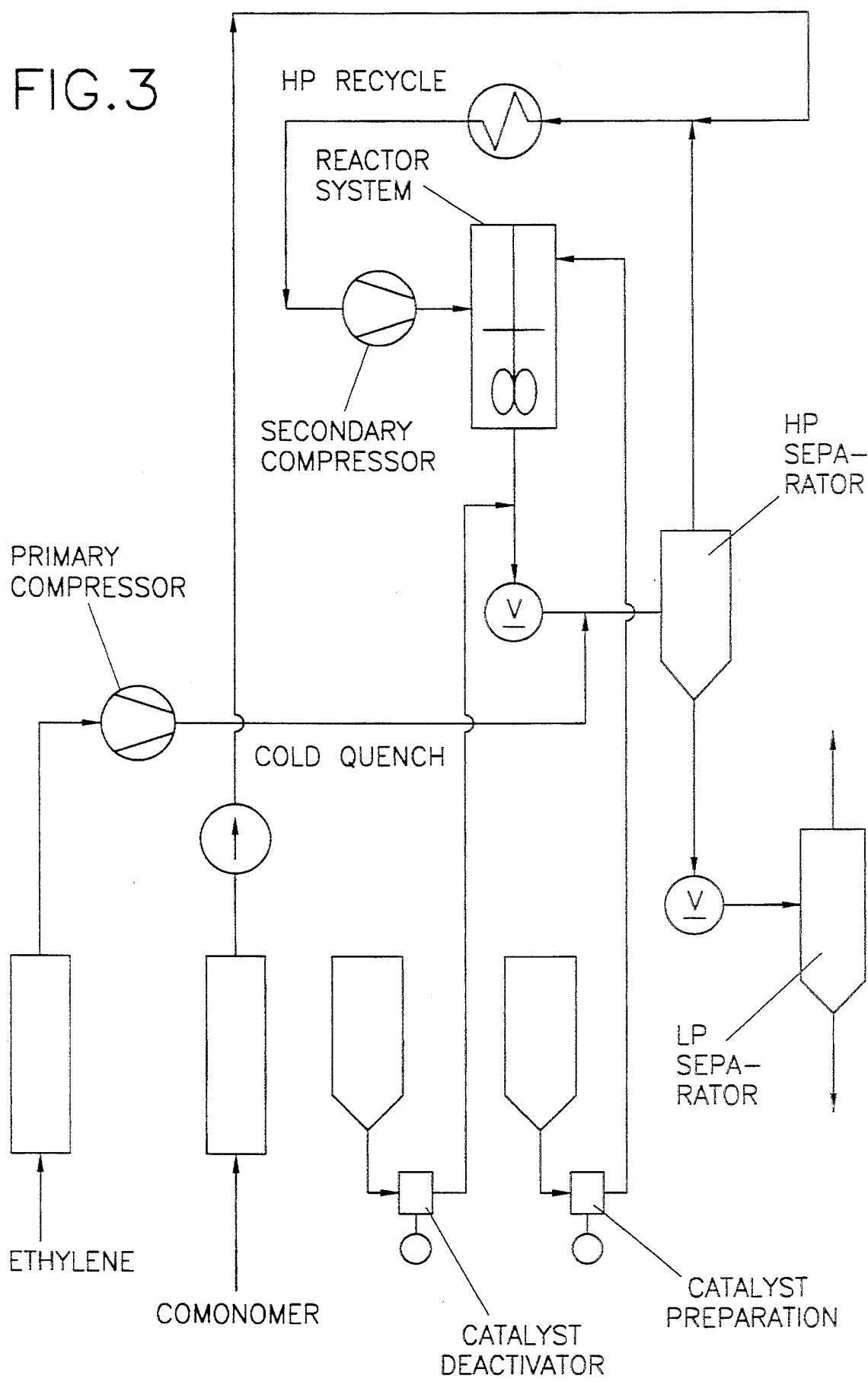

HIGH TEMPERATURE POLYMERIZATION PROCESS USING IONIC CATALYSTS TO PRODUCE POLYOLEFINS

CROSS REFERENCE TO RELATED APPLICATIONS

This application is a continuation-in-part of U.S. Ser. No. 07/898,638, filed Jun. 15, 1992, now abandoned, which is a continuation-in-part of Ser. No. 07/737,611, filed Jul. 30, 1991 now issued as U.S. Pat. No. 5,198,401, which is a continuation-in-part of Ser. No. 07/555,977, filed Jul. 19, 1990, abandoned, which is a continuation-in-part of Ser, No. 133,480, filed Dec. 22, 1987, abandoned, which is a continuation-in-part of Ser. No. 07/8,800 filed Jan. 30, 1987, abandoned; a continuation-in-part of Ser. No. 07/875,165, filed Apr. 28, 1992, now issued as U.S. Pat. No. 5,278,119, a continuation-in-part of Ser. No. 07/133,052, filed Dec. 21, 1987, abandoned, which is a continuation-in-part of Ser. 07/011,471, filed Jan. 30, 1987, abandoned; and, a continuation-in-part of Ser. No. 07/542,236, filed Jun. 22,1990.

FIELD OF THE INVENTION

This invention relates to an improved polymerization process. Particularly, this invention provides a high temperature process for polymerizing ethylenically unsaturated olefin(s) or unsaturated monomer(s), including cyclic monomers, either alone or in combination with other monomers, in a polymerization medium at elevated pressures. More specifically, this invention relates to a process for polymerizing olefins at high pressures in a polymerization medium at high temperature utilizing an ionic olefin polymerization catalyst derived from the reaction of a cyclopentadienyl-containing transition metal compound having a hydrolyzable alkyl or hydride ligand with an ion exchange activator composition as described in copending U.S. patent application Ser. No. 542,236 and U.S. Pat. Nos. 5,198,401 and 5,278,119 all incorporated by reference. The ionic catalyst system has been found to be highly active at temperatures of 160° C. or greater, and provides a process capable of producing polymer products of desired chemical and physical properties at a greater production rate than possible with alumoxane activated catalyst systems heretofore used under similar temperature and pressure conditions. In the process of the invention separation of polymer product from the polymerization medium with recycle of the medium for reuse in polymer production is economically simplified.

BACKGROUND OF THE INVENTION

Polyolefins, particularly polyethylene, polypropylene and α-olefin copolymers of ethylene and propylene, have heretofore been produced by a variety of processes ranging from solvent, slurry and gas phase polymerization processes which are carried out over wide ranges of temperature and pressure. The polymerization reaction of such processes have been conducted with a wide range of catalyst compositions ranging from conventional Ziegler-Natta type catalyst systems to alumoxane activated metallocene catalyst systems as described in European Patent No. 0,129,368 to the more recently disclosed ionic catalyst systems as described in European Patent Applications 0 277 004 and 0 277 003.

In solvent processes, polymerization of monomers occurs in the medium of a solvent, typically an inert hydrocarbon such as hexane, heptane, toluene or the like, which carries the catalyst into contact with monomer dissolved therein and typically the medium is one in which the product polymer is soluble. The solvent medium absorbs the heat generated by the polymerization reaction and control of the solvent medium temperature controls the temperature of reaction whereby optimum productivity or polymer properties may be achieved according to the characteristic of the catalyst used. After polymer production, the solvent medium and dissolved polymer must be separated, by a subsequent processing step, as by evaporation.

In slurry processes, monomer polymerization occurs in the medium of a fluid in which the polymer product is insoluble or poorly soluble and, as the polymer is produced, it precipitates or beads up in the medium while unreacted monomer remains in fluid form. The temperature of reaction is controlled by controlling the temperature of the slurry medium. The medium must be separated from the polymer product by a subsequent processing step. In those situations wherein the slurry medium is an inert normally liquid hydrocarbon compound distinct from the monomer itself, subsequent separation from the polymer product is accomplished by evaporation or filtration. When the medium for slurry. polymerization is the monomer itself produced by subjugation of the monomer to high pressures to convert it to a fluid form, separation of unreacted monomer medium from the polymer product is typically accomplished by causing the fluidized monomer to vaporize, or flash off, from the non-volatile polymer product. The unreacted monomer may be caused to flash off by significantly reducing its pressure or by adding additional heat to the medium, or both. Generally, because slurry polymerization processes are carried out at a temperature in the monomer reaction medium of less than about 80° C., flashing of the unreacted monomer medium from the polymer product is accomplished by addition thereto of heat rather than by significant reduction of pressure as this would require significant costly recompression of recovered monomer before recycle to the reactor.

Whether a solvent or slurry procedure is used, ultimately the produced polymer must be separated from the polymerization medium which is generally accomplished by addition thereto of extra heat, which adds to the cost of polymer production.

The need to separate the solvent or slurry medium is a disadvantage in terms of the subsequent processing required. However, a solvent or slurry medium method of polymer production does enable one to control the temperature of the polymerization reaction to achieve the set of chemical and physical properties desired in the polymer product as those product characteristics are dictated by the nature of the polymerization catalyst system which is used.

The physical and chemical properties obtained in the polymer product, i.e., of molecular weight, molecular weight distribution, comonomer content and distribution, tacticity, etc., are significantly influenced by the type of catalyst system utilized, which in turn often dictates the nature of the polymerization process employed. Conventional Ziegler-Natta type catalysts, which comprise a Group IV-B metal compound and a metal alkyl cocatalyst such as an aluminum trialkyl, are highly active multi-sited catalysts which generally produce polymer products of a high molecular weight and broad molecular weight distribution. On the other hand, an alumoxane activated metallocene catalyst is a single sited catalyst system which generally produces a polymer of a narrow molecular weight distribution which may be of a relatively high molecular weight, particularly wherein the metallocene component is one of a Group IVB transition metal, particularly titanium or zirconium. However, to obtain a useful level of productivity with an alumoxane activated metallocene system when utilized in a solvent or slurry polymerization process, it is generally necessary to employ the alumoxane component in an amount such that the catalyst system has an aluminum atom to transition metal atom ratio of at least 1000:1, and typically much greater—i.e., 10,000:1 or greater. Lesser ratios, such as 12:1 to 100:1, can be employed such as that described in U.S. Pat. No. 4,752,597.

Although an alumoxane activated metallocene catalyst system has a variety of advantages relative to a conventional Ziegler-Natta type catalyst system, to be sufficiently active, such catalyst systems require the presence of a quantity of alumoxane which is undesirable in terms of the catalyst cost and the catalyst residue imparted into the polymer product produced therewith. As a consequence, a catalyst system has been developed wherein a transition metal component is activated to a catalytic state by reaction with certain types of ion exchange compositions, as described in commonly owned copending U.S. patent application Ser. Nos. 542,236 U.S. Pat. Nos. 5,198,401 and 5,278,119 and since described in European Patent Applications 0 277 003 and 0 277 004. Such ionic catalyst system are single-sited catalyst systems which produce polymers of a narrow molecular weight distribution at high levels of productivity wherein the ratio of ionic activator component to transition metal component is 1:1 or less. The transition metal component of such catalyst systems—like those in an alumoxane activated system—contains at least one ligand in the nature of a pi-bonding moiety, eg., a cyclopentadienyl group, hence may be referred to as a metallocene type catalyst system. In comparison to a conventional Ziegler-Natta catalyst the ionically activated metallocene catalyst system provides the same advantages of an alumoxane activated metallocene catalyst system while overcoming one of the aspects of an alumoxane activated system which was undesirable, namely the use of an excessive amount of costly alumoxane cocatalyst which also imparts a high content of catalyst residue to the polymer produced with a metallocene catalyst system.

For many applications it is of primary importance for a polyolefin to have a relatively high weight average molecular weight while having a relatively narrow molecular weight distribution. A high weight average molecular weight, accompanied by a narrow molecular weight distribution, provides a polyolefin or an ethylene-α-olefin copolymer with high strength properties. Generally, a desire for a polyolefin of this combination of properties dictates the use of a single sited metallocene-type catalyst system.

When an alumoxane activated metallocene catalyst system is employed, it has been found that a zirconium metallocene species is commonly more active than a hafnium or titanium analog for the polymerization of ethylene alone or together with another α-olefin to produce a copolymer. When employed in a non-supported form—i.e., as a homogenous or soluble catalyst system—in an alumoxane activated system it has been found that only the zirconium or hafnium species of a metallocene may be used wherein the reactor pressure exceeds about 500 bar (50 MPa; 7,252 psi) and reaction temperature exceeds 100° C. (212° F.). At such pressures and temperatures, the titanium species of metallocenes as activated by an alumoxane are generally unstable unless they are deposited upon a catalyst support.

Typically, the productivity of an alumoxane activated catalyst system is significantly greater in a solvent or slurry phase polymerization procedure than is the productivity of the same metallocene-alumoxane catalyst system when utilized in a high temperature and high pressure polymerization process.

For many reasons it is desirable to produce a polymer by a procedure wherein the temperature of the medium within which monomer polymerization occurs is as high as possible—i.e., a polymerization temperature greater than that of melting point and approaching the decomposition temperature of the product polymer. One reason for this desire is that increasing temperature should increase the rate of polymerization, which in turn would increase the rate of polymer production within a given unit of time. This would increase the capacity of a given reactor system for the production of polymer product. Another reason, particularly when a polymerization diluent is used as the medium in which polymerization occurs, is the simplification of treatment following polymer production to separate and recover the medium from the polymer product. In this case after polymer production the medium would comprise the polymerization diluent and unreacted monomers which may be separated from the polymer product by allowing the medium to flash off, or vaporize away from the non-volatile polymer, for recovery as a vapor to be condensed for reuse by recycle back to reactor. If polymerization could practically be accomplished while the medium is already at or in excess of its flash point temperature, then the medium would not need to be heated after removal from the reactor in order to separate and recover it from the polymer product. Since the heat of reaction of the polymerization reaction could be utilized as the source for heating the polymerization medium, the cost of extrinsically heating to subsequently flash the medium from the polymer product could be saved, again decreasing product cost.

Even when a diluent is not used and the polymerization medium is comprised of one or more monomers maintained in a fluid state by application of high pressures, it would still be desirable to conduct the polymerization reaction at a high temperature to increase the rate of polymer production. Further, wherein the product is a copolymer one monomer of which is of low volatility, i.e., a monomer of from $C_4$ to $C_{20a}$, higher temperature for the polymerization medium would allow unreacted low volatility monomer to be flashed away from the polymer product with a slight pressure reduction and no or little additional heat input to the medium following its removal from the reactor.

To realize the desirable benefits which could stem from a high temperature of the polymerization medium requires the development of a catalyst system which is not adversely affected in its performance with respect to polymer productivity or polymer properties by a high temperature of the polymerization medium.

Heretofore, U.S. Pat. No. 5,084,534 has described the use of an alumoxane activated metallocene catalyst system for use in a high pressure—high temperature process for production of narrow molecular weight distribution polyolefin products. Unlike a relatively low temperature solution or slurry polymerization process wherein to achieve greater levels of productivity required increasing quantities of alumoxane to metallocene, in U.S. Pat. No. 5,084,534 it was found that under high temperature—high pressure polymerization conditions (i.e., at least 120° C.; 248° F.—500 bar; 50 MPa; 7,252 psi) the maximum level of catalyst productivity was instead achieved by limiting the quantity of alumoxane to an amount no greater than to provide the catalyst system with an Al:transition metal atom ratio of 1000:1 or less. By such limitation, when used in a high pressure-high temperature process the metallocene-alumoxane catalyst system is stated to have a high productivity—defined as 1000 g polymer/g catalyst or greater—the highest productivity exemplified being 4800 g polymer/g catalyst.

That level of catalyst productivity that may be achieved as a maximum in a high pressure-high temperature process as described by U.S. Pat. No. 5,084,534, is achieved at a temperature below that which is most desirable for process optimization in terms of medium-polymer separation, unreacted monomer recovery and reuse recycle operation. It has been found that in a high pressure polymerization process practiced in accordance with U.S. Pat. No. 5,084,534, that the metallocene-alumoxane catalyst productivity increases with temperature up to a range of about 140° C. to about 160° C. and thereafter declines significantly and rapidly with further increases of temperature of the polymerization medium. Accordingly, to maintain the reaction conditions at the state most favorable to maximum polymer productivity by the metallocene-alumoxane catalyst, the polymerization medium must be maintained at a controlled temperature by limiting catalyst concentration or by heat exchange so that the medium does not exceed a temperature of about 140° C. to about 160° C. Further, at this temperature, to flash unreacted monomer away from the polymer product without significantly reducing its pressure requires additional heat input to the medium after its removal from the reaction zone. The need to keep the medium at or below about 160° C. during the polymerization reaction and thereafter to additionally heat it to flash and recover unreacted monomer from the product polymer without significant pressure reduction adds significantly to the cost of polymer production.

Though the benefits of polymerization at high temperatures—approaching that of the decomposition point of the product polymer—are apparent, to date no catalyst system has been found to be of practical use at such high temperatures wherein the desired product is a polyolefin of narrow molecular weight distribution and relatively high molecular weight. A need still exists for a polymerization process capable of attaining a high temperature in the polymerization medium which retains the several advantages heretofore achieved with single sited metallocene catalyst systems while enabling the efficient and economically attractive production of high molecular weight polymer products at high levels of productivity based upon the amount of catalyst employed.

SUMMARY OF THE INVENTION

This invention comprises the discovery that an ionic olefin polymerization catalyst is capable of maintaining a high level of productivity for olefin polymerization at temperatures of 140° C. (284° F.), preferably 160° C. (320° F.) and greater, namely temperatures exceeding that of the melting point temperature and approaching that of the polymer product decomposition temperature. This discovery provides for a process for polymerizing ethylenically unsaturated monomers at high rates of polymer production, particularly olefins, alone or in combination with other comonomers, at high temperatures and high pressures (i.e., 500 up to 5000 bars; 50 up to 500 MPa; 7,252 up to 72,520 psi) in the presence of a polymerization medium comprising a diluent or, preferably a normally gaseous monomer, particularly ethylene, which is maintained in a fluid state. By practice of this process the capacity of a reactor for polymer production is increased compared to that which heretofore was possible under the same pressure with an alumoxane activated metallocene catalyst system. Additionally separation of the polymerization medium, particularly unreacted monomer, from the polymer product is rendered more economical, thereby further reducing polymer production cost.

With the use of an ionic catalyst system as described the process comprises; in a polymerization reaction zone, contacting one or more olefin(s) with an ionic catalyst composition which is carried in a polymerization medium while at a temperature of from about 1.40° C. (320° F.) to about 300° C. (572° F.), or greater, while a pressure within the reaction zone is maintained of at least about 500 bars (50 MPa), wherein the polymerization medium comprises a diluent or the polymerization medium consists essentially of one or more olefin(s) one of which is a normally gaseous olefin which is maintained in a fluidize state. The process further comprises the step of maintaining contact of the olefin or monomer with the ionic catalyst for a time sufficient to produce a polyolefin having a weight average molecular weight of at least about 10,000, removing polymerization medium from the reaction zone, and flashing off the polymerization medium to isolate polymer product and recover unreacted olefin or monomer for reuse by recycle to the reaction zone. Because the reaction medium is allowed to attain a high temperature by absorbing the heat of the polymerization reaction the bulk of the unreacted monomer content of the medium may be flashed off of the polymer product with little reduction of its pressure and with little or no additional heat input and recovered for recycle use with significantly reduced need for recompression of the unreacted monomer before recycle.

In accordance with the present invention, the foregoing advantages are preferably accomplished by polymerizing ethylene, at elevated temperatures and pressures; either as ethylene alone or in combination with other monomers such as α-olefins having from 3–18 carbon atoms, i.e., butene-1, hexene-1, octene-1, 4-methylpentene-1, decene-1 and norbornene and di-olefins having 4–18 carbon atoms, i.e., 1,3-butadiene, 1,4-hexadiene, 4-methyl-1,4-hexadiene, 5-methyl-1,4-hexadiene, 1,7-octadiene, ethylidiene norbornene and norbornadiene; in the presence of a medium containing a catalyst system comprising a cyclopentadienyl-containing transition metal compound having a hydrolyzable ligand and an ionic exchange activator composition as described in copending U.S. patent application Ser. No. 542,236 and U.S. Pat. Nos. 5,198,401 and 5,278,119. As indicated more fully hereinafter, it is important, in the process of this invention, that the temperature of the medium be allowed to reach at least about 140° C., preferably 160° C. and greater, but without exceeding the decomposition temperature of the polymer product and that the polymerization pressure be at least about 500 bar (50 MPa). Use of scavenging agents to enhance catalyst productivity may optionally be employed in the described process.

BRIEF DESCRIPTION OF THE DRAWINGS

FIG. 3 is a schematic representation of the polymerization of olefins in a continuous high pressure pilot plant.

DETAILED DESCRIPTION OF THE PREFERRED EMBODIMENTS

Figure 1:
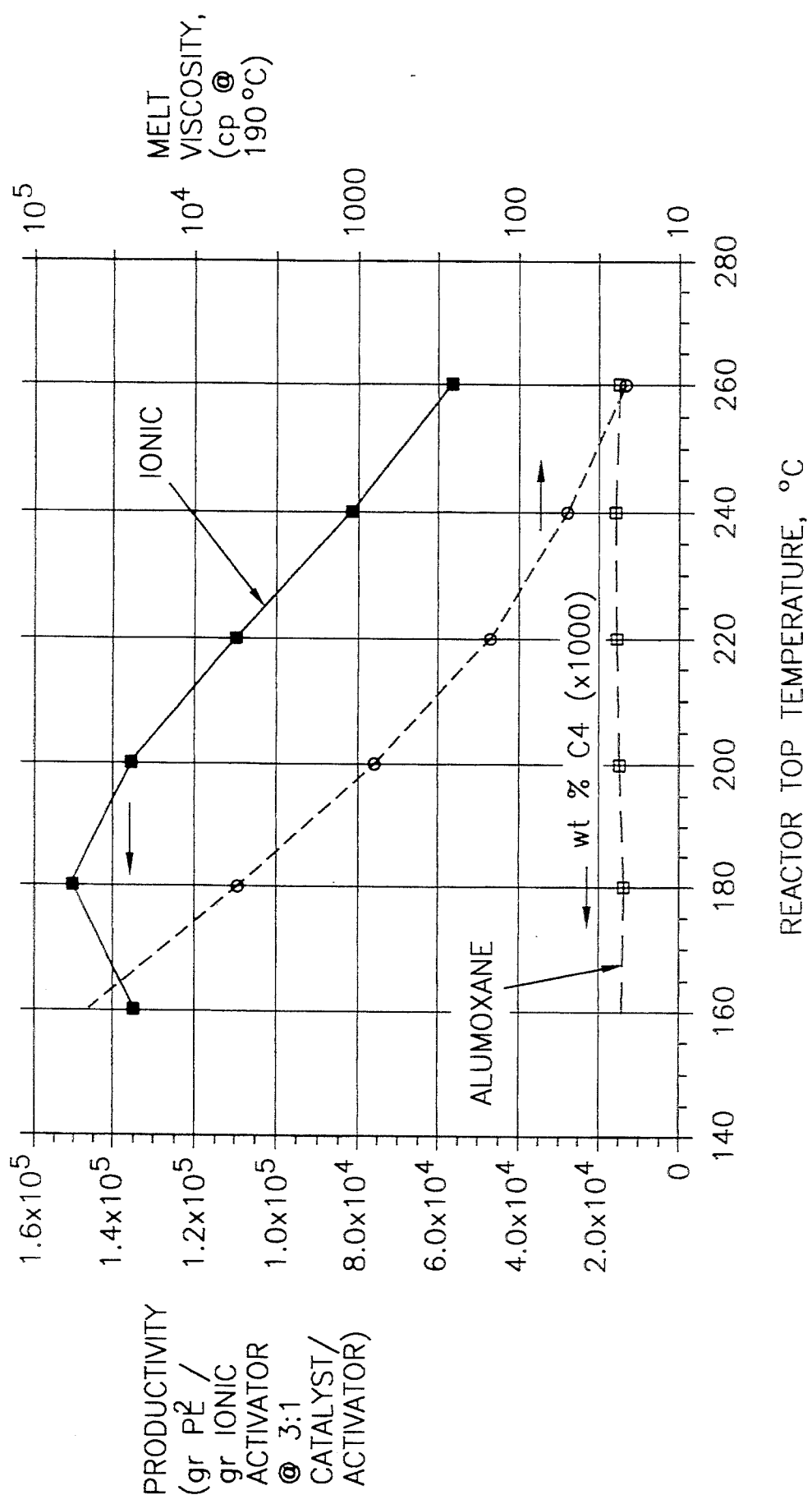
FIG. 1 illustrates catalyst productivity.

The invention in its preferred embodiment relates to an improved process for polymerizing olefins, particularly ethylene, either alone or in combination with other monomers such as α-olefins and di-olefins, in the presence of a catalyst comprising a cyclopentadienyl-transition metal compound and an ionic exchange composition at elevated temperatures and pressures. The polymerization is accomplished at a temperature above the melting point of the polymer product but below the decomposition temperature of said polymer product and at a pressure equal to or above about 500 bar (50 MPa).

By the process of this invention, ethylene, either alone or together with α-olefins having 3 or more carbon atoms or di-olefins having 4 or more carbon atoms, is polymerized in a reaction medium which attains the high temperature by reason of absorbing the heat generated by the polymerization reaction. According to this invention, one can also produce olefin copolymers particularly copolymers of ethylene and higher α-olefins having from 3–18 carbon atoms and copolymers of ethylene and di-olefins having from 4 to 18 carbon atoms. The comonomer content of a copolymer can be controlled through the selection of the transition metal compound component of the ionic catalyst and by controlling the partial pressure of the various monomers.

Ionic Catalyst System—General Description

In general any ligand stabilized hydrolyzable di- or poly-alkyl or hydride complex of a transition metal may be converted into a reactive coordinatively unsaturated alkyl or hydride cationic complex by reaction with an activator composition as described hereafter. The cationic transition metal complex is catalytically active for polymerization of ethylenically unsaturated monomers such as ethylene, propylene, butene-1 and ethylenically unsaturated aromatic monomers such as styrene.

The ionic catalysts preferred for use in this invention are formed from a transition metal compound containing at least one ligand in the nature of a cyclopentadienyl group, as such or as forming part of a polycyclic ligand group. The preferred ionic catalyst can be represented by one of the following general formulae (all references to Groups being the new group notation of the Periodic Table of the Elements as described by *Chemical and Engineering News*, 63(5), 27, 1985):

1. $\{[(A\text{—}Cp)MX_1]^+\}_d\{[B']^{d-}\}$
2. $\{[(A\text{—}Cp)MX_1L']^+\}_d\{[B']^{d-}\}$

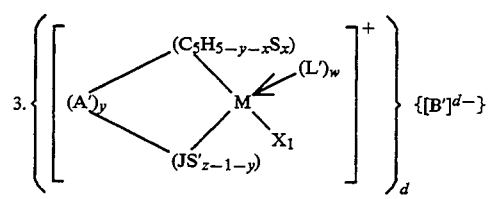

(A-Cp) is either (Cp)(Cp*) or Cp-A'-Cp*; Cp and Cp* are the same or different cyclopentadienyl ring substituted with from zero to five substituent groups S, each substituent group S being, independently, a radical group which is a hydrocarbyl, substituted-hydrocarbyl, halocarbyl, substituted-halocarbyl, hydrocarbyl-substituted organometalloid, halocarbyl-substituted organometalloid, disubstituted boron, disubstituted pnictogen, substituted chalcogen or halogen radicals, or Cp and Cp* are cyclopentadienyl rings in which any two adjacent S groups are joined forming a $C_4$ to $C_{20}$ ring to form a saturated or unsaturated polycyclic cyclopentadienyl ligand;

A' is a bridging group, which group may serve to restrict rotation of the Cp and Cp* rings or $(C_5H_{5-y-x}S_x)$ and $(JS'_{z-1-y})$ groups;

$(C_5H_{5-y-x}S_x)$ is a cyclopentadienyl ring substituted with from zero to five S radicals:

x is from 0 to 5 denoting the degree of substitution;

M is titanium, zirconium or hafnium;

$X_1$ is hydride radical, hydrocarbyl radical, substituted-hydrocarbyl radical, hydrocarbyl-substituted organometalloid radical or halocarbyl-substituted organometalloid radical which radical may optionally be covalently bonded to both or either M and L' or all or any M, S or S';

$(JS'_{-1-y})$ is a heteroatom ligand in which J is an element from Group 15 of the Periodic Table of Elements with a coordination number of 3 or an element from Group 16 with a coordination number of 2 and may contain cyclic substituents thereon; S' is a radical group which is a hydrocarbyl, substituted hydrocarbyl, halocarbyl, substituted halocarbyl, hydrocarbyl-substituted organometalloid, or halocarbyl-substituted organometalloid; and z is the coordination number of the element J;

y is 0 or 1;

L' is an olefin, diolefin or aryne ligand, or an other neutral Lewis base; L' can also be a second transition metal compound of the same type such that the two metal centers M and M* are bridged by $X_1$ and $X'_1$, wherein M* has the same meaning as M and $X'_1$ has the same meaning as $X_1$ where such dimeric compounds which are precursors to the cationic portion of the catalyst are represented by the formula:

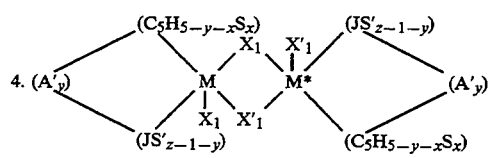

w is an integer from 0 to 3;

B' is a chemically stable, non-nucleophilic anionic complex having a molecular diameter about or greater than 4 angstroms; and d is an integer representing the charge of B'.

The ionic catalysts are prepared by combining at least two components. In one preferred method, the first component is a cyclopentadienyl derivative of a Group 4 metal compound containing at least one ligand which will combine with the second component or at least a portion thereof such as a cation portion thereof. The second component is an ion-exchange compound comprising a cation which will irreversibly react with at least one ligand contained in said Group 4 metal compound (first component) and a non-coordinating anion which is either a single coordination complex comprising a plurality of lipophilic radicals covalently coordinated to and shielding a central formally charge-bearing metal or metalloid atoms or an anion comprising a plurality of boron atoms such as polyhedral boranes, carboranes and metallacarboranes.

The cation portion of the second component may comprise Bronsted acids such as protons or protonated Lewis bases or may comprise reducible Lewis acids such as ferricinum, tropylium, triphenylcarbonium or silver cations.

In general, suitable anions for the second component may be any stable and bulky anionic complex having the following molecular attributes: 1) the anion should have a molecular diameter greater than 4 Å; 2) the anion should form stable ammonium salts; 3) the negative charge on the anion should be delocalized over the framework of the anion or be localized Within the core of the anion; 4) the anion should be a relatively poor nucleophile; and 5) the anion should not be a powerful reducing or oxidizing agent. Anions meeting these criteria—such as polynuclear boranes, carboranes, metallocarboranes, polyoxoanions and anionic coordination complexes are well described in the chemical literature. Upon combination of the first and second components, the second component reacts with one of the ligands of the first component, thereby generating an ion pair consisting of a Group 4 metal cation and the aforementioned anion, which anion is compatible with and noncoordinating towards the Group 4 metal cation formed from the first component. The anion of the second compound must be capable of stabilizing the Group 4 metal cation without interfering with the Group 4 metal cations ability to function as a catalyst and must be sufficiently labile to permit displacement by an olefin, diolefin or an acetylenically unsaturated monomer during polymerization.

A. Transition Metal Component

The transition metal compounds preferred for use as first compounds in the preparation of the ionic catalyst are cyclopentadienyl derivatives of titanium, zirconium and hafnium, represented by the following general formulae:

5. $(A—Cp)MX_1X_2$
6. $(A—Cp)ML$
7. $(Cp^*)(CpR)MX_1$

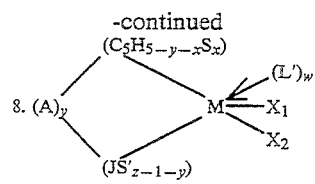

8.

wherein:
(A-Cp) is either (Cp) (Cp*) or Cp-A'-Cp*; Cp and Cp* are the same or different cyclopentadienyl rings substituted with from zero to five substituent groups S, each substituent group S being, independently, a radical group which is a hydrocarbyl, substituted-hydrocarbyl, halocarbyl, substituted-halocarbyl, hydrocarbyl-substituted organometalloid, halocarbyl-substituted organometalloid, disubstituted boron, disubstituted pnictogen, substituted chalcogen or halogen radical, or Cp and Cp* are cyclopentadienyl rings in which any two adjacent S groups are joined forming a $C_4$ to $C_{20}$ ring to give a saturated or unsaturated polycyclic cyclopentadienyl ligand;

R is a substituent on one of the cyclopentadienyl radicals which is also bonded to the metal atom;

A' is a bridging group, which group may serve to restrict rotation of the Cp and Cp* rings or $(C_5H_{5-y-x}S_x)$ and $JS'_{(z-1-y)}$ groups;

y is 0 or 1;

$(C_5H_{5-y-x}S_x)$ is a cyclopentadienyl ring substituted with from zero to five S radicals;

x is from 0 to 5 denoting the degree of substitution;

$(JS'_{z-1-y})$ is a heteroatom in which J is an element from Group 15 of the Periodic Table of Elements with a coordination number of 3 or an element from Group 16 with a coordination number of 2; S' is a radical group which is a hydrocarbyl, substituted hydrocarbyl, halocarbyl, substituted halocarbyl, hydrocarbyl-substituted organometalloid, or halocarbyl-substituted organometalloid; and z is the coordination number of the element J;

L is an olefin, diolefin, or aryne ligand;

L' is an olefin, diolefin or aryne ligand, or a neutral Lewis base; L' can also be a second transition metal compound of the same type such that the two metal centers M and M* are bridged by $X_1$ and $X'_1$, wherein M* has the same meaning as M and $X'_1$ has the same meaning as $X_1$ where such dimeric compounds which are precursors to the cationic portion of the catalyst are represented by the formula:

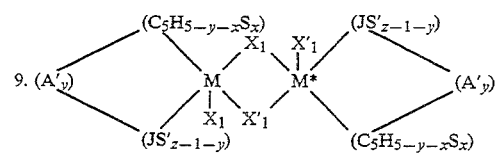

9.

w is an integer from 0 to 3; and $X_1$ and $X_2$ are, independently, hydride radicals, hydrocarbyl radicals, substituted hydrocarbyl radicals, halocarbyl radicals, substituted halocarbyl radicals, and hydrocarbyl- and halocarbyl-substituted organometalloid radicals; or $X_1$ and $X_2$ are joined and bound to the metal atom to form a metallacycle ring containing from about 3 to about 20 carbon atoms; or $X_1$ and $X_2$ together can be an olefin, diolefin or aryne ligand.

Table 1 depicts representative constituent moieties for the metallocene components of formulae 6–9. The list is for illustrative purposes only and should not be construed to be limiting in any way. A number of final components may be formed by permuting all possible combinations of the constituent moieties with each other. Illustrative compounds of the formula 6 type are bis (cyclopentadienyl)hafnium dimethyl, ethylenebis(-tetrahydroindenyl)zirconium dihydride, bis(pentamethyl)zirconium ethylidene, dimethylsilyl (1-fluorenyl)-(cyclopentadienyl)titanium dimethyl and the like. Illustrative compounds of the formula 7 type are: bis(cyclopentadienyl)(1,3-butadiene)zirconium, bis(cyclopentadienyl)(2,3-dimethyl- 1,3-butadiene)zirconium, bis(-pentamethylcyclopentadienyl)(benzyne)zirconium, bis(pentamethylcyclopentadienyl)titanium ethylene and the like. Illustrative compounds of the formula 8 type are: (pentamethylcyclopentadienyl)(tetramethylcyclopentadienylmethylene)zirconium hydride, (pentamethylcyclopentadienyl) (tetramethylcyclopentadienyl-methylene)hafnium benzyl, (pentamethylcyclopentadienyl) (tetramethyicyclopentadienylmethylene) zirconium phenyl and the like. Illustrative compounds of the formula 9 type are: dimethylsilyl(tetramethylcyclopentadienyl) (t-butylamido)zirconiumdimethyl, ethylene (methylcyclopentadienyl)(phenylamido)titanium dimethyl, methylphenylsilyl(indenyl) (phenyphosphido) hafnium dihydride and (pentamethylcyclopentadienyl) (di-t-butylamido)hafnium dimethyl.

For illustrative purposes, the above compounds from Table 1 do not include the neutral Lewis base ligands (L'). The conditions under which complexes containing neutral Lewis base ligands such as ether or those which form dimeric compounds is determined by the steric bulk of the ligands about the metal center. For example, the t-butyl group in Me$_2$Si(Me$_4$C$_5$)(N-t-Bu)ZrCl$_2$ has greater steric requirements than the phenyl group in Me$_2$Si(Me$_4$C$_5$)(NPh)ZrCl$_2$ùEt$_2$O thereby not permitting ether coordination in the former compound in its solid state. Similarly, due to the decreased steric bulk of the trimethyisilylcyclopentadienyl group in [Me$_2$Si(-Me$_3$SiC$_5$H$_3$)(N-t-Bu)ZrCl$_2$]$_2$ versus that of the tetramethylcyclopentadienyl group in Me$_2$Si(Me$_4$C$_5$)(N-t-Bu)ZrCl$_2$, the former compound is dimeric and the latter is not.

B. The Activator Component

Ionic catalysts can be prepared by reacting a transition metal compound with some neutral Lewis acids, such as B(C$_6$F$_5$)$_3$, which upon reaction with the hydrolyzable ligand (X) of the transition metal compound forms an anion, such as ([B(C$_6$F$_5$)$_3$(X)]−), which stabilizes the cationic transition metal species which is generated by the reaction. Ionic catalysts can be, and preferably are, prepared with activator components which are ionic compounds or compositions.

Compounds useful as an activator component in the preparation of the ionic catalyst system used in the process of this invention comprise a cation, which may be a Bronsted acid capable of donating a proton, and a compatible noncoordinating anion which anion is relatively large (bulky), capable of stabilizing the active catalyst species (the Group 4 transition metal cation) which is formed when the two compounds are combined and said anion will be sufficiently labile to be displaced by olefinic diolefinic and acetylenically unsaturated substrates or other neutral Lewis bases such as ethers, nitriles and the like. Three classes of compatible non-coordinating anion compositions have been disclosed in copending U.S. patent application No. 542,236 and U.S. Pat. Nos. 5,198,401 and 5,278,119: 1) anionic coordination complexes comprising a plurality of lipophilic radicals covalently coordinated to and shielding a central charge-bearing metal or metalloid core; 2) anions comprising a plurality of boron atoms such as carboranes, metallacarboranes and boranes; and 3) polyanionic compositions wherein a plurality of either of the above two types of non-coordinating anions are covalently bonded to an atomic, molecular or polymeric complex or particle (T) which forms the central core of the polyanionic composition.

In general, the activator compounds containing single anionic coordination complexes which are useful in this invention may be represented by the following general formula:

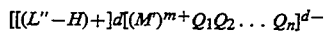   10.

wherein:

H is a hydrogen atom;

[L"−H] is a Bronsted acid;

M' is a metal or metalloid;

Q$_1$ to Q$_n$ are, independently hydride radicals, bridged or unbridged dialkylamido radicals, alkoxide and aryloxide radicals, hydrocarbyl and substituted-hydrocarbyl radicals, halocarbyl and substituted-halocarbyl radicals and hydrocarbyl and halocarbyl-substituted organometalloid radicals and any one, but not more than one, of Q$_1$ to Q$_n$ may be halide radicals;

m is an integer representing the formal valence charge of M'; and n is the total number of ligands Q.

Any metal or metalloid capable of forming an anionic complex which is lo stable in water may be used or contained in the anion of the second compound. Suitable metals then, include, but are not limited to, aluminum, gold, platinum and the like. Suitable metalloids include, but are not limited to, boron, phosphorus, silicon and the like. Compounds containing anions which comprise coordination complexes containing a single metal or metalloid atom are, of course, well known and many, particularly such compounds containing a single boron atom in the anion portion, are available commercially. In light of this, salts containing anions comprising a coordination complex containing a single boron atom are preferred.

The preferred activator compounds comprising boron may be represented by the following general formula:

   11.

wherein:

B is boron in a valence state of 3;

Ar$_1$ and Ar$_2$ are the same or different aromatic or substituted-aromatic hydrocarbon radicals containing from about 6 to about 20 carbon atoms and may be linked to each other through a stable bridging group; and X$_3$ and X$_4$ are, independently, hydride radicals, hydrocarbyl and substituted-hydrocarbyl radicals, halocarbyl and substituted-halocarbyl radicals, hydrocarbyl and halocarbyl-substituted organometalloid radicals, disubstituted pnictogen radicals, substituted chalcogen radicals and halide radicals, with the proviso that $X_3$ and $X_4$ will not be halide at the same time.

In general, $Ar_1$ and $Ar_2$ may, independently, be any aromatic or substituted-aromatic hydrocarbon radical. Suitable aromatic radicals include, but are not limited to, phenyl, naphthyl and anthracenyl radicals. Suitable substituents on the substituted-aromatic hydrocarbon radicals, hydrocarbyl radicals, include, but are not necessarily limited to, hydrocarbyl radicals, organo metalloid radicals, alkoxy and aryloxy radicals, alkylamido radicals, fluorocarbyl and fluorohydrocarbyl radicals and the like such as those useful as $X_3$ and $X_4$. The substituent may be ortho, meta or para, relative to the carbon atoms bonded to the boron atom. When either or both $X_3$ and $X_4$ are a hydrocarbyl radical, each may be the same or a different aromatic or substituted-aromatic radical as the $Ar_1$ and $Ar_2$, or the same may be a straight or branched alkyl, alkenyl or alkynyl radical, a cyclic hydrocarbon radical or an alkyl-substituted cyclic hydrocarbon radical. $X_3$ and $X_4$ may also, independently be alkoxy of dialkylamido radicals wherein the alkyl portion of said alkoxy and dialkylamido radicals, hydrocarbyl radicals and organometalloid radicals and the like. As indicated above, $Ar_1$ and $Ar_2$ could be linked to either $X_3$ or $X_4$. Finally, $X_3$ and $X_4$ may also be linked to each other through a suitable bridging group.

The most preferred activator compounds comprising boron may be represented by the following general formula:

$$[L''-H]+[B(C_6F_5)_3Q]- \qquad 12.$$

wherein:

F is fluorine, C is carbon and B, [L''—H], and Q are defined hereinabove. Illustrative but not limiting, examples of most preferred activator compounds comprising boron which may be used in the preparation of the improved catalysts of this invention include N,N-dialkylanilinium salts (L'=N,N-dialkylaniline where Q is a simple hydrocarbyl such as methyl, butyl, cyclohexyl, or phenyl or where Q is a polymeric hydrocarbyl of indefinite chain length such as polystyrene, polyisoprene, or polyparamethylstyrene. Polymeric Q substituents on the most preferred anion offer the advantage of providing a highly soluble ion-exchange activator component and final ionic catalyst. Soluble catalysts and/or precursors are often preferred over insoluble waxes, oils, phases, or solids because they can be diluted to a desired concentration and can be transferred easily using simple equipment in commercial processes.

Activator components based on anions which contain a plurality of boron atoms may be represented by the following general formulae:

$$[L''-H]_d[(CX)_a(BX')_mX''_b]^{c-} \qquad 13.$$

or $$[L''-H]_{d'}[[[(CX_6)_{a'}(BX_7)_{m'}(X_8)_{b'}]^{c'-}]_2M''^{n'+}]^{d-} \qquad 14.$$

wherein:

[L''—H] is either H+ or a Bronsted acid derived from the protonation of a neutral Lewis base;

C is carbon; B is boron;

X, X', X'', $X_6$, $X_7$ and $X_8$ are, independently, hydride radicals, halide radicals, hydrocarbyl radicals, substituted-hydrocarbyl radicals, halocarbyl radicals, substituted-halocarbyl radicals, or hydrocarbyl or halocarbyl-substituted organometalloid radicals;

M'' is a transition metal;

a and b are integers $\geq 0$; c is an integer $\geq 1$; a+b+c=an even numbered integer from 2 to about 8; and m is an integer ranging from 5 to about 22;

a° and b' are the same or a different integer; c' is an integer $\geq 2$; a'+b'+c'=an even-numbered integer from 4 to about 8; m' is an integer from 6 to about 12; n' is an integer such that 2c'=n'=d'; and d' is an integer $\geq 1$.

Preferred anions comprising a plurality of boron atoms are:

(1) A trisubstituted ammonium salt of a borane or carborane anion satisfying the general formula:

$$[(CH)_{ax}(BH)_{bx}]^{cx-} \qquad 15.$$

wherein;

ax is either 0 or 1; cx is either 1 or 2; ax+x=2; and bx is an integer ranging from about 10 to 12;

(2) A trisubstituted ammonium salt of a borane or carborane or a neutral borane or carborane compound satisfying the general formulae:

$$[(CH)_{ay}(BH)_{my}(H)_{by}]^{cy-} \qquad 16.$$

wherein:

ay is an integer from 0 to 2; by is an integer from 0 to 3; cy is an integer from 0 to 3; ay+by+cy=4; and my is an integer from about 9 to about 18; or (3) A trisubstituted ammonium salt of a metallaborane of metallacarborane anion satisfying the following general formula:

$$[[[(CH)_{az}(BH)_{mz}(H)_{bz}]^{cz-}]_2M''^{nz+}]^{dz-} \qquad 17.$$

wherein:

az is an integer from 0 to 2; bz is an integer from 0 to 2; cz is either or 3; mz is an integer from about 9 to 11; az+bz+cz=4; and nz and dz are, respectively, 2 and 2 or 3 and 1.

The activator composition most preferred for forming the ionic catalyst used in this process are those containing a tetrapentafluorophenyl boron anion or two or more tripentafluorophenyl boron anion groups covalently bound to a central atomic, molecular or polymeric complex or particle. Other examples of activator specific compositions which may be used to form an anionic catalyst useful in this invention are identified and more fully described in European Patent applications 0 277 003 and 0 277 004.

As indicated, the ionic catalyst compositions used in the present invention will, preferably, be prepared in a suitable solvent or diluent. Suitable solvents or diluents include any of the compound known in the prior art to be useful in the polymerization of olefins, diolefins and acetylenically unsaturated monomers. Suitable compounds for preparation of the ionic catalyst, then, include, but are not necessarily limited to, straight and branched-chain hydrocarbons such as isobutane, lo butane, pentane, hexane, heptane, octane and the like; cyclic and alicyclic hydrocarbons such as cyclohexane, cycloheptane, methylcyclohexane, methylcycloheptane and the like and aromatic and alkyl-substituted aromatic compounds such as benzene, toluene, xylene and the like. Suitable compounds also include liquid or liquified olefins which thereafter may act as monomers or comonomers including ethylene, propylene, butadiene, cyclopentene, hexene-1,3-methyl-1-pentene, 4-methyl-1-pentene, 1,4-hexadiene, octene-1, decene-1, styrene and the like. Suitable compounds for catalyst preparation further include basic solvents which are not generally useful as polymerization solvents when conventional Ziegler-Natta type polymerization catalysts are used, such as chlorobenzene.

The active species of the catalyst with which this process invention is practiced is relatively stable and is not subject to a decline in activity or deactivation at temperatures exceeding 160° C. as are alumoxane cocatalyzed metallocene catalyst systems. Unlike metallocene-alumoxane catalyst systems wherein, to obtain a practical level of catalyst productivity it is generally required to use an amount of alumoxane, measured as aluminum atom, to provide a ratio of Al:transition metal well in excess of 1000:1; ionic catalysts used in the process of this invention are highly productive when prepared at molar ratios of cation, or metallocene, to anion, or activator, of 10:1 to about 1:1, preferably about 3:1 to 1:1.

The Polymerization Process

In accordance with this invention one can produce high molecular weight polymer products at high temperatures. Temperature does not constitute a limiting parameter in the process of this invention as with the prior art metallocene/alumoxane catalyst. The ionic catalyst systems described herein, therefore, are suitable for the polymerization of olefins over a wide range of temperatures and pressures. In the process of this invention the temperature of the medium within which the polymerization reaction occurs is at least 140° C. (284° F.) and preferably above about 160° C. (320° F.) and may range to about 350° C. (662° F.), but below the decomposition temperature of said polymer product, typically from about 310° C. (590° C) to about 325° C. (536° F.). Preferably, the polymerization is completed at a temperature within the range from about 180° C. to about 280° C. As also indicated, the polymerization is completed at a pressure above about 500 bar (50 MPa), and generally at a pressure lo within the range from about 500 bar to about 3500 bar (350 MPa). Preferably, the polymerization is completed at a pressure within the range from about 800 bar (80 MPa) to about 1500 bar (150 MPa).

In its most preferred embodiments, the process of this invention is carried out as a continuous process wherein as polymerization medium containing polymer product and catalyst is removed from the reaction zone fresh catalyst and monomer and, wherein a polymerization diluent is used, fresh diluent, are added to the reaction zone in corresponding amounts to maintain an equilibrium of mass within the reaction zone. In the continuous process unreacted monomer and/or diluent are recovered from the polymer product by flash evaporation, conditioned for reuse and recycled to the reaction zone as at least a part of the makeup amounts of monomer and/or diluent feed to the reaction zone. To save cost of recompression of recovered monomer it is preferably flashed away from the product polymer by only a slight reduction of pressure, or, alternatively with no reduction of pressure by the addition of moderate amounts of additional heat to the medium during the flash recovery operation. Wherein a polymerization diluent is used as the medium, the bulk of unreacted monomer is preferably recovered separately from the diluent by a first high pressure flashing operation and the diluent, together with small amounts of unreacted monomer, is next recovered by total pressure reduction on the medium.

The temperature to which the polymerization medium may be heated by the heat of the polymerization reaction in part depends on the volume of the medium in relationship to the amount of catalyst concentration and if the medium is a diluent then the amount of monomer concentration therein. Both the catalyst and monomer should be supplied to the reaction zone in amounts sufficient to provide for a heat of reaction from the polymerization process which will cause the polymerization medium to heat to and be maintainable at a temperature of at least 140° C. or greater, as desired. Temperature control of the reaction medium may be readily exercised by controlling the concentration of catalyst supplied to the reaction zone.

The catalyst may be prepared in an a hydrocarbon solution and metered into the fluid polymerization medium or reaction zone in this form. Alternatively, the catalyst components may be added to the reaction zone as separate streams and the catalyst system allowed to form in situ in the reaction zone.

The polymer product obtained in accordance with this invention will have a weight average molecular weight in the range of about 10,000 to about 1,500,000 and preferably 80,000 to about 1,000,000. The polydispersities (molecular weight distribution) expressed as $M_w/M_n$ typically range from 1.5 to 3.0. In those situations wherein the molecular weight of the polymer product that would be produced at a given set of operating conditions would be higher than desired, any of the techniques known in the prior art for control of molecular weight, such as the use of hydrogen, may be used in the process of this invention. If no hydrogen is used during the polymerization the polymers may contain chain end unsaturation. The polymers produced by the process of this invention are capable of being fabricated into a wide variety of articles, as is known for homopolymers of ethylene and copolymers of ethylene and higher $\alpha$-olefins.

The Process Reaction Medium

As indicated, the polymerization of monomers occurs in a medium which carries the ionic catalyst into contact with the monomer and absorbs the heat of reaction liberated by monomer polymerization. The polymerization medium may comprise a normally liquid inert hydrocarbon compound or the medium may consist essentially of a normally gaseous monomer which under application of pressure is maintained in a supercritical fluid state within the reaction zone. Generally, wherein a normally liquid inert hydrocarbon is used to provide the reaction medium, the polymerization reaction may be carried out at lower pressures than required when the polymerization medium consists essentially of a fluidized monomer.

Inert hydrocarbon compounds which may be used as a polymerization diluent to provide the polymerization medium include aliphatic, cycloaliphatic, and aromatic hydrocarbons having from six to twenty carbon atoms. Suitable diluents include hexane, cyclohexane, heptane, methylcyclohexane, octane, toluene, xylene and the like. The temperature chosen for the most optimum practice of the process is in part governed by the type of polymerization medium used and the type of comonomer used if an ethylene copolymer product is being produced. Wherein comonomers of a diluent are used which are themselves of relatively high volatility then lower reaction temperatures may be used while still obtaining satisfactory post reaction flashing of the unreacted comonomer and/or diluent medium away from the product polymer compared to the case wherein a diluent or comonomer of low volatility is used. As indicated, the reaction is preferably carried out at a minimum polymerization temperature of 160° C., which is more than adequate to flash off comonomers of high volatility with only small reductions of pressure, after the recovery of which the diluent may be flashed off for separate recovery by full reduction of pressure.

In this situation, the ability of the inventive process to polymerize monomer to polyolefin product at high levels of productivity at a temperature of at least 160° C. and even higher provides greater economy for the polymer production process. In this process the catalyst can be supplied to the reaction zone in greater concentrations to produce more polymer with greater heat liberation to the medium without significantly adverse affects on catalyst productivity due to higher medium temperatures which otherwise would require a metallocene-alumoxane catalyst to be supplied to the medium at lower catalyst concentrations to maintain the reaction at a lower temperature to obtain optimum productivity of the metallocene-alumoxane catalyst. As diluents or comonomers of lower volatility are used, which require greater heat levels for satisfactory post reaction flashing off from the polymer, in the inventive process the temperature of reaction may beneficially be allowed to range to levels approaching that of the polymer decomposition temperature. The processing economics realized thereby are increased polymer production due to increased catalyst concentration, accompanied by a satisfactory post reaction flashing off of the medium to recover polymer product without the need for significant pressure reduction or additional post reaction heat input to accomplish the flashing. Again, unreacted monomer may be recovered without significant pressure reduction, slightly recompressed and then recycled to the reactor for reuse. The diluent may be separately recovered by full pressure reduction after unreacted monomer is recovered.

More preferably, the process is practiced with a polymerization medium which consists essentially of one or more monomers maintained by pressure in a supercritical fluid state. Although this entails a greater degree of initial monomer compression and compression cost, this method of practice is preferred because no portion of the reactor volume is occupied by an inert diluent compound. Thus, with the same reactor, a greater level of throughput of polymer production can be realized than when an inert diluent is used as the polymerization medium.

In the monomer-supercritical-fluid mode of practice, the quantity of monomer which remains unreacted following polymerization is separated from polymer product by flashing without significant pressure reduction, the unreacted monomer is recovered, slightly recompressed as necessary and recycled back to the reactor for further use. Most desirably unreacted monomer is flashed off of the polymer product without significant reduction of its pressure by first routing the medium to a high pressure separator. Accordingly, it is preferred to run the polymerization reaction at as high a medium temperature as possible, i.e., no greater than the polymer decomposition temperature, to enable the bulk of the medium, consisting of unreacted monomer, to be flashed away from the polymer with only a slight reduction of pressure. This permits the unreacted monomer to be recovered for recycle back to the reactor after only slight recompression, a significant cost savings in the economics of the process which may be accomplished with a small amount of additional heat input to the medium after its removal from the reaction zone.

Copending U.S. Ser. No. 770,499 illustrates use of monocyclopentadienyl transition metal metallocenes and MAO in a high pressure reactor process.

EPA 277004, example 27 and EPA 277003, example 32 illustrate use of a high pressure batch reactor (as compared to continuous reactor), employing an ionically activated catalyst system to form polymer product. The catalyst productivity noted in these runs were 44.5 and 295 kg PE/note catalyst respectively.

FIG. 1 illustrates catalyst productivity obtained with an ionically activated catalyst system versus an alumoxane activated catalyst system.

Figure 2:
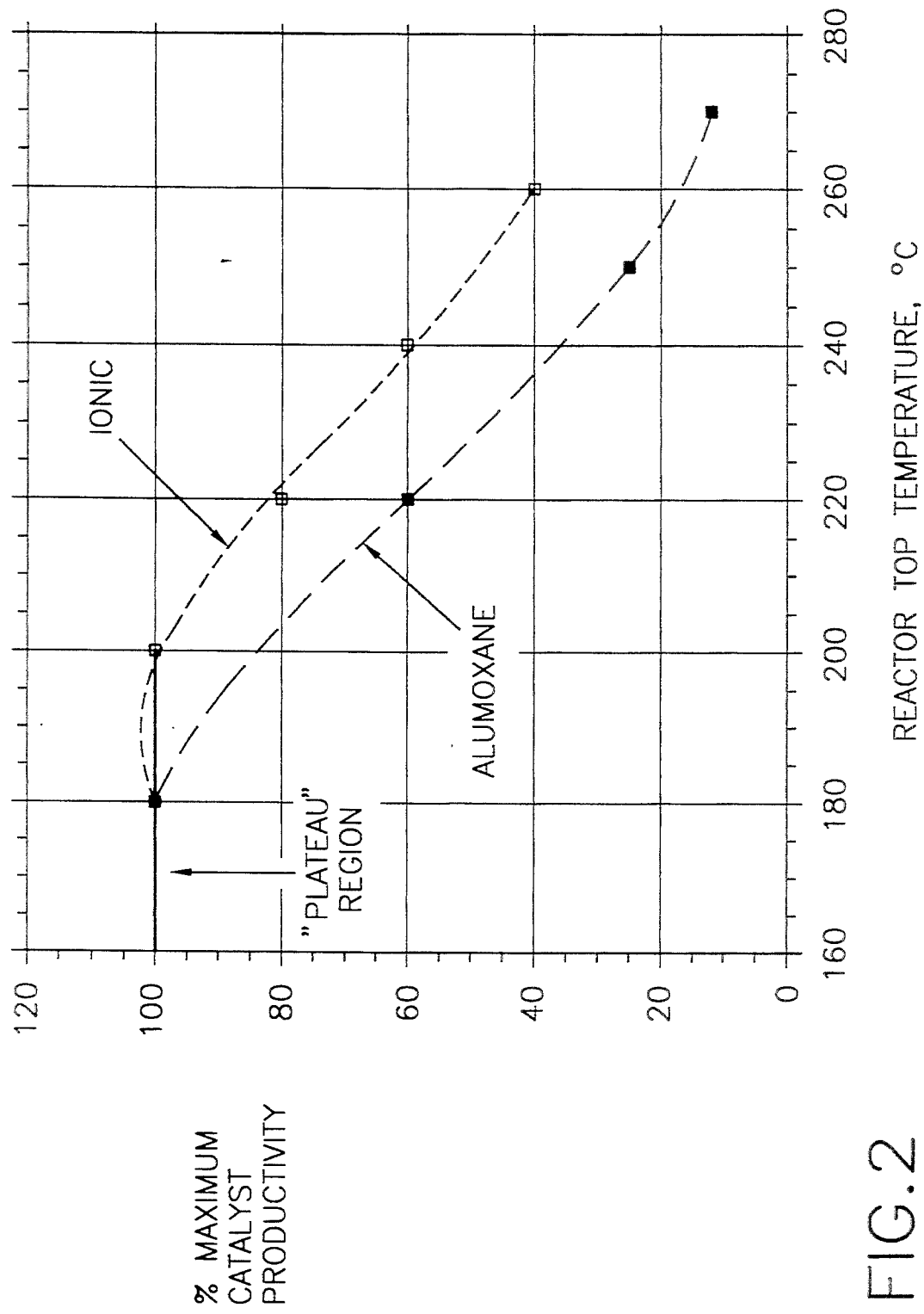
FIG. 2 illustrates catalyst temperature performance.

FIG. 2 compares temperature performance of ionic versus alumoxane activated catalyst systems. Those data found in FIG. 2 indicate a gain in temperature stability for the ionic catalyst system relative to the alumoxane activated system.

As shown in FIG. 2, reactor outlet temperatures greater or equal than 200° C. were reached with the ionically activated catalyst system while maintaining catalyst productivity levels about or greater than 100 kg PE/gr activator. It was noticed that catalyst productivity deteriorated at above about 235° C. The product Mw dropped with increasing temperature from 20,000 Mw at 183° C. to 1863 Mw at 269° C. The weight % butene-1 incorporated varied with temperature, with a maximum of 19% at 234° C. This reflects a change in comonomer reactivity ratio with temperature for this catalyst system. The product MWD was narrow (2.1–2.5) at all temperatures, as expected for single-sited catalysts.

A comparison between the temperature performance of ionically activated metallocene and the same metallocene activated by methylalumoxane (MAO) is shown in FIG. 2. As indicated, with MAO, the catalyst productivity begins to drop at reactor outlet temperatures around 175° C. whereas, with the ionic activator, the metallocene shows the same effect around 200° C. There is, therefore, a significant gain in terms of catalyst thermal stability when employing the ionic activator.

EXAMPLES

Polymerization Conditions

Polymerizations were carried out in a high-pressure (HP) pilot plant equipped to perform continuous Ziegler polymerization reactions at pressures up to 3000 barg and temperatures up to 300° C. The polymerizations were conducted adiabatically in a 4-ltr autoclave reactor maintained at a constant pressure of 1300 barg and at a outlet temperature ranging from 170° to 270° C. The reactor content was mixed at 1800 rpm with a stirrer and a motor. The reactor was divided in two equal zones by an horizontal baffle mounted on the stirrer shaft. The temperature in each zone was continuously recorded with thermocouples. The feed gas was introduced in the top reactor zone at a constant temperature of 30° C. The temperature difference between the reactor outlet and the feed gas is directly proportional to the monomer conversion or yield in the reactor (about 1% per 12.5° C.). (See FIG. 3)

The facility has, downstream of the autoclave reactor, a letdown valve (LDV) for reducing the pressure and allowing the monomers to be separated from the polymer melt in a high pressure separator (HPS). Between the LDV and the HPS, there is a heat exchanger for heating or cooling the monomer/polymer mixture emerging from the reactor. The polymer melt is taken from the HPS to the low pressure separator (LPS), whereas the monomers are recycled to the reactor via the high pressure recycle system consisting of a series of coolers, polymer knockout vessels and a high pressure compressor which supplies the monomer feed to the autoclave reactor. In the LPS, the polymer melt is further depressurized to close to atmospheric pressure, allowing more residual monomers to be flashed out. From the LPS, the polymer melt is pumped by a gear pump through a double-hole die plate, and the resulting polymer strands cooled in water and pelletized.

To compensate for the monomer loss due to polymerization in the reactor, purified compressed ethylene was added upstream of the HPS and purified compressed butene-1 at the entrance of the high pressure recycle system.

The molar ratio of ethylene to comonomer in the reactor was held constant during the polymerization experiments by controlling the fresh ethylene to fresh butene-1 mass flow rate ratio and the operating conditions of the HPS.

Catalyst System Preparation

Catalyst solution was prepared by mixing specified amounts of solid transition metal component and ionic activator into a known volume of purified toluene under inert ($N_2$) atmosphere at a controlled temperature (20° C.). The stirred catalyst vessel was made of transparent plexiglass, which allowed visual inspection of each catalyst solution. All catalyst solutions appeared yellow and homogeneous after addition of the catalyst components in toluene. The catalyst solution was continuously fed by a high pressure pump into the reactor at a rate which resulted in the desired top reactor temperature. The catalyst vessel was equipped with a closed-loop recirculation system for improved homogenization of its content.

Exact run conditions including catalyst preparation [transition metal (TM) concentration (g/ltr), ionic activator concentration (g/ltr), and (TM/activator) molar ratio, the reactor top and bottom temperature (°C.), the fresh butene-1 to fresh ethylene mass flow rate ratio ($C_4/C_2$), the catalyst productivity (kg PE/gr activator) and polymer characteristics including viscosity (centipoise at 190° C.), and weight percent butene-1 (determined by $^1$H-NMR)] are given in Table 2.

EXAMPLES 1-6

Examples 1-6 were performed in the HP continuous facility described hereabove with a silicon-bridged bis-Cp zirconocene, and the ionic activator, A. The catalyst solution was prepared by mixing 1.55 gr zirconocene and 1.0 gr activator A with 1 liter purified toluene in the catalyst vessel described above. The polymerizations were performed at a constant pressure of 1300 barg and a constant fresh butene-1 to ethylene mass flow ratio of 0.47. No solvent was added. The reactor top temperature was controlled by the catalyst flow rate and held constant during each test. The production rate varied between 15 and 20 kg PE/hr.

EXAMPLE 7

This polymerization was conducted under the conditions described in Table 1 with a silicon-bridged bis-Cp hafnocene and the ionic activator, C. An exceptionally high temperature rise (from 160° to 220° C.) was observed across the reactor with this catalyst system, reflecting the high thermal stability of the active catalyst species at those conditions. A VLDPE copolymers of 52,000 Mw containing 19.4 weight % butene-1 was produced at a catalyst productivity of 60 kg PE/gr activator.

As one skilled in the art will appreciate, the above specification describes the invention with particular reference to those modes now contemplated as best for its practice but without intent to limit the invention with respect to variations which from this description will be apparent or obvious to those skilled in the art, all of which are intended to be within the scope and spirit of this invention as described above and claimed hereafter.

TABLE 1

| A' | Cp, Cp*, CpR or $(C_5H_{(5-y-z)}S_z)$ | $(JS'_2)$ | $X_1$ or $X_2$ | M |
|---|---|---|---|---|
| dimethylsilyl | cyclopentadienyl | t-butylamide | hydride | zirconium |
| diethylsilyl | methylcyclopentadienyl | phenylamido | methyl | hafnium |
| di-n-propylsilyl | 1,2-dimethylcyclopentadienyl | p-n-butylphenylamido | ethyl | titanium |
| diisopropylsilyl | 1,3-dimethylcyclopentadienyl | cyclohexylamido | phenyl | L or L' |
| di-n-butylsilyl | indenyl | perflurophenylamido | fluoro | ethylene |
| di-t-butylsilyl | 1,2-diethylcyclopentadienyl | n-butylamido | bromo | propylene |
| di-n-hexylsilyl | tetramethylcyclopentadienyl | methylamido | iodo | t-butene |
| methylphenylsilyl | ethylcyclopentadienyl | ethylamido | n-propyl | 1,4-hexadiene |
| ethylmethylsilyl | n-butylcyclopentadienyl | n-propylamido | isopropyl | 1,3-butadiene |
| diphenylsilyl | cyclohexylmethylcyclopentadienyl | isopropylamido | n-butyl | 1,3-hexadiene |
| di(p-t-butylphenethylsilyl) | n-octylcyclopentadienyl | benzylamido | amyl | acetylene |
| n-hexylmethylsilyl | β-phenylpropylcyclopentadienyl | t-butylphosphido | isoamyl | ethylacetylene |
| cyclopentamethylenesilyl | tetrahydroindenyl | ethylphosphido | hexyl | benzyne |
| cyclotetramethylenesilyl | propylcyclopentadienyl | phenylphosphido | isobutyl | L' |
| cyclotrimethylenesilyl | t-butylcyclopentadienyl | cyclohexylphosphido | heptyl | diethylether |
| dimethylgermanyl | benzylcyclopentadienyl | oxo | octyl | dimethylether |
| diethylgermanyl | diphenylmethylcyclopentadienyl | sulfido | nonyl | trimethylamine |
| phenylamido | trimethylgermylcyclopentadienyl | $(JS_{z-1})$ | decyl | tripheylamine |
| t-butylamido | trimethylstannylcyclopentadienyl | methoxide | cetyl | triethylamine |
| methylamido | triethylplumbylcyclopentadienyl | ethoxide | methylidene (both x) | triphenylphosphine |
| t-butylphosphido | trifluoromethylcyclopentadienyl | methylthio | ethylidene (both x) | tetrahydrofuran |
| ethylphosphido | trimethylsilylcyclopentadienyl | ethylthio | propylidene (both x) | thiophene |

TABLE 1-continued

| | | | |
|---|---|---|---|
| phenylphosphido methylene | pentamethylcyclopentadienyl (when y = 0) | dimethylamido | dimethylsulfide |
| dimethylmethylene | fluorenyl | diphenylamido | |
| diethylmethylene | octahydrofluorenyl | methylphenylamido | |
| ethylene | N,N-dimethylamidocyclopentadienyl | dicyclohexylphosphido | |
| dimethylethylene | dimethylphosphidocyclopentadienyl | diphenylphosphido | |
| diethylethylene | methoxycyclopentadienyl | bis(trimethylallyl)amido | |
| dipropylethylene | dimethylboridocyclopentadienyl | trimethylsilyloxide | |
| propylene | (N,N-dimethylamidomethyl)cyclopentadienyl | | |
| dimethylpropylene | tetrafluorocyclopentadienyl | | |
| diethylpropylene | | | |
| 1,1-dimethyl-3,3-dimethylpropylene | | | |
| tetramethyldisiloxane | | | |
| 1,1,4,4-tetramethyl-disilylethylene | | | |

TABLE 2

| Example | TM/ activator | TM (gr/ltr) | Activator (gr/ltr) | TM/activator mole ratio | top/btm rxn T C | C4/C2 wt ratio | catalyst productivity Kg PE/gr activator | viscosity cp @ 190 C. | wt % C4 H-NMR |
|---|---|---|---|---|---|---|---|---|---|
| 1 | B/A | 1.6 | 1.0 | 3.0 | 160/183 | 0.47 | 100 | 22510 | 15.1 |
| 2 | B/A | 1.6 | 1.0 | 3.0 | 180/199 | 0.47 | 150 | 5350 | 15.9 |
| 3 | B/A | 1.6 | 1.0 | 3.0 | 200/215 | 0.47 | 127 | 750 | 16.8 |
| 4 | B/A | 1.6 | 1.0 | 3.0 | 220/234 | 0.47 | 110 | 147 | 19.0 |
| 5 | B/A | 1.6 | 1.0 | 3.0 | 240/251 | 0.47 | 78 | 50 | 18.2 |
| 6 | B/A | 1.6 | 1.0 | 3.0 | 260/269 | 0.47 | 51 | 21 | 17.2 |
| 7 | D/C | 3.7 | 1.2 | 3.0 | 160/221 | 0.40 | 60 | | 19.4 |

ABBREVIATIONS:
A = N,N,-dimethylanilinium tetrakis(pentafluorophenyl) boron (Mw = 801.23)
B = dimethylsilylbis(4,5,6,7 tetrahydro-indenyl) zirconium dimethyl (Mw = 415.7)
C = tri(pentafluorophenyl) boron (Mw = 511.8)
D = dimethylsilylbis(4,5,6,7 tetrahydro-indenyl) hafnium dimethyl (Mw = 503)

We claim:

1. A process for polymerizing one or more monomers from the group consisting of olefins, diolefins and acetylenically unsaturated monomers, comprising contacting at a temperature up to about 300° C. and a pressure from above about 500 bar to about 3445 bar in a suitable solvent or diluent, said monomers with an active polymerization catalyst comprising a cation of a mono- or bis(cyclopentadienyl) derivative of a group IV-B metal, and a compatible non-coordinating anion comprising boron or a plurality of boron atoms, said anion being sufficiently labile to permit displacement by said monomers.

2. The process of claim 1, wherein the catalyst system comprises one 20 or more of:

(1) $\{[(A\text{—}Cp)MX_1]^+\}_d\{[B']^{d-}\}$
(2) $\{[(A\text{—}Cp)MX_1L']^+\}_d\{[B']^{d-}\}$

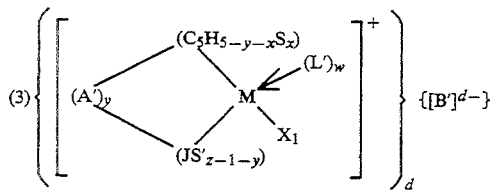

$$(3)\left\{\left[\begin{array}{c}(C_5H_{5-y-x}S_x)\\(A')_y\quad M\quad (L')_w\\(JS'_{z-1-y})\quad X_1\end{array}\right]^+ \{[B']^{d-}\}\right\}_d$$

wherein:

(A-Cp) is either (Cp) (Cp*) or Cp-A'-Cp*; Cp and Cp* are the same or different cyclopentadienyl ring substituted with from zero to five substituent groups S, each substituent group S being, independently, a radical group which is a hydrocarbyl, substituted-hydrocarbyl, halocarbyl, substituted-halocarbyl, hydrocarbyl-substituted organometalloid, halocarbyl-substituted organometalloid, disubstituted boron, disubstituted pnictogen, substituted chalcogen or halogen radical, or Cp and Cp* are cyclopentadienyl rings in which two adjacent S groups are joined forming a $C_4$ to $C_{20}$ ring to form a saturated or unsaturated polycyclic cyclopentadienyl ligand;

A' is a bridging group which restricts rotation of the Cp and Cp* rings or $(C_5H_{5-y-x}S_x)$ and $(JS'_{z-1-y})$ groups;

$(C_5H_{5-y-x}S_x)$ is a cyclopentadienyl ring substituted with from zero to five S radicals;

x is from 5 to 0 denoting the degree of substitution;

M is titanium, zirconium or hafnium;

$X_1$ is hydride radical, hydrocarbyl radical, substituted-hydrocarbyl radical, hydrocarbyl-substituted organometalloid radical or halocarbyl-substituted organometalloid radical which radical may optionally be covalently bonded to both or either M and L' or all or any M, S or S';

$(JS'_{z-1-y})$ is a heteroatom ligand in which J is an element from Group 15 of the Periodic Table of Elements with a coordination number of 3 or an element from Group 16 with a coordination number of 2; S' is a radical group which is a hydrocarbyl, substituted hydrocarbyl, halocarbyl, substituted halocarbyl, hydrocarbyl-substituted organometalloid, or halocarbyl-substituted organometalloid; and z is the coordination number of the element J;

y is 0 or 1;

L' is an olefin, diolefin, aryne ligand, or an other neutral Lewis base or a second transition metal compound of the same type such that the two metal centers M and M* are bridged by $X_1$ and $X'_1$, wherein M* has the same meaning as M and $X'_1$ has the same meaning as $X_1$ where such dimeric compounds which are precursors to the cationic transition metal species of the catalyst are represented by the formula:

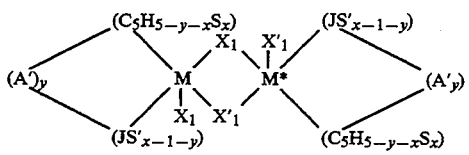

wherein:

w is an integer from 0 to 3;

B' is a chemically stable, non-nucleophilic anionic complex having a molecular diameter about or greater than 4 angstroms; and d is an integer representing the charge of B'.

3. The process of claim 1, wherein said solvent or diluent consists essentially of one or more polymerizable olefin(s).

4. The process of claim 1, wherein said α-olefin comprises ethylene.

5. The process of claim 1, wherein ethylene is polymerized in combination with another olefin selected from the group consisting of $C_{3-18}$ olefins, $C_{4-18}$ dienes, $C_{4-18}$ cyclic olefins or diolefins, $C_{4-18}$ aromatic containing olefins.

6. The process of claim 2, wherein $[B']^{d-}$ is represented by the formula:

$$[(M')^{m+}Q_1Q_2 \ldots Q_n]^{d-}$$

wherein:

M' is a metal or metalloid;

$Q_1$ to $Q_n$ are, independently, hydride radicals, bridged or unbridged, dialkylamido radicals, alkoxide and aryloxide radicals, hydrocarbyl and substituted-hydrocarbyl radicals, halocarbyl and substituted-halocarbyl radicals and hydrocarbyl and halocarbyl-substituted organometalloid radicals and any one, but not more than one, of $Q_1$ to $Q_n$ may be halide radicals;

m is an integer representing the formal valence charge of M'; and n is the total number of ligands Q.

7. The process of claim 6, wherein $[B']^{d-}$ is represented by the formula:

$$[BAr_1Ar_2X_3X_4]-$$

wherein:

B is boron in a valence state of 3;

$Ar_1$ and $Ar_2$ are the same or different aromatic or substituted-aromatic hydrocarbon radicals containing from about 6 to about 20 carbon atoms and may be linked to each other through a stable bridging group; and $X_3$ and $X_4$ are, independently, hydride radicals, hydrocarbyl and substituted-hydrocarbyl radicals, halocarbyl and substituted-halocarbyl radicals, hydrocarbyl and halocarbyl-substituted organometalloid radicals, disubstituted pnictogen radicals, substituted chalcogen radicals and halide radicals, with the proviso that $X_3$ and $X_4$ will not both be halide.

8. The process of claim 7, wherein $[B']^{d-}$ is represented by the formula:

$$[B(C_6F_5)_3Q]-$$

wherein:

F is fluorine, C is carbon, B is boron and Q is a hydride radical, bridged or unbridged dialkylamido radical, alkoxide or aryloxide radical, hydrocarbyl or substituted-hydrocarbyl radical, halocarbyl or substituted-halocarbyl radical, hydrocarbyl or halocarbyl-substituted organometalloid radical, or halide radical.

9. The process of claim 8, wherein Q is a pentafluorophenyl radical.

10. The process of claim 9, wherein Q is a polymeric hydrocarbyl radical.

11. The process of claim 2, wherein $[B']^{d-}$ is tetrapentafluorophenyl boron.

12. The process of claim 2, wherein $[B']^{d-}$ is represented by:

$$[(CX)_a(BX')_mX''_b]^{c-}$$

or $$[[[(CX_6)_{a'}(BX_7)_{m'}(X_8)]^{c'-}]_2M''^{n'+}]^{d'}$$

wherein:

C is carbon; B is boron;

X, X', X", $X_6$, $X_7$ and $X_8$ are, independently, hydride radicals, halide radicals, hydrocarbyl radicals, substituted-hydrocarbyl radicals, halocarbyl radicals, substituted-halocarbyl radicals, or hydrocarbyl or halocarbyl-substituted organometalloid radicals;

M" is a transition metal;

a and b are integers $\geq 0$; c is an integer $\geq 1$; a+b+c- =an even integer from 2 to about 8; and m is an integer ranging from 5 to about 22;

a' and b' are the same or a different integer; c' is an integer $\geq 2$; a'+b'+c'=an even-numbered integer from 4 to about 8; m' is an integer from 6 to about 12; n' is an integer such that 2c'=n'=d'; and d' is an integer $\geq 1$.

13. The process of claim 1, wherein the said solvent or diluent is maintained at a temperature of about 180° C. to about 280° C.

14. The process of claim 1 wherein a molar ratio of cation to anion is in the range of 10:1 to about 1:1.

15. The process of claim 14 wherein the ratio is in the range of about 1 to about 1:1.

16. The process of claim 1 wherein the catalyst system is formed in-situ with the solvent or diluent.

17. The process according to claim 1 or 2 wherein said cyclopentadienyl derivative of a group IV-B metal comprises two cyclopentadienyl rings bound to the metal.

18. The process according to claim 1 or 2 wherein said cyclopentadienyl derivative of a group IV-B metal comprises a single cyclopentadienyl ring bound to the metal.

* * * * *

UNITED STATES PATENT AND TRADEMARK OFFICE
CERTIFICATE OF CORRECTION

PATENT NO. : 5,408,017
DATED : April 18, 1995
INVENTOR(S) : Howard W. Turner, Jo Ann M. Canich, Bernard J. Folie It is certified that error appears in the above-indentified patent and that said Letters Patent is hereby corrected as shown below:

Column 21, line 46, in Claim 2, delete the number "20" following the phrase "comprises one".

Signed and Sealed this

Seventeenth Day of October, 1995

Attest:

BRUCE LEHMAN

Attesting Officer     Commissioner of Patents and Trademarks